United States Patent [19]

Quinn, III

[11] 4,114,293
[45] Sep. 19, 1978

[54] FRAME FOR FACIAL IDENTIFICATION SYSTEM WITH COMPONENT RESERVOIR

[76] Inventor: William T. Quinn, III, 681 Park Ave., Freehold, N.J. 07728

[21] Appl. No.: 832,045

[22] Filed: Sep. 9, 1977

[51] Int. Cl.² ............................................. G09B 1/30
[52] U.S. Cl. ...................................... 35/28; 40/10 D
[58] Field of Search .................... 35/28; 40/10 D, 13, 40/155; 248/441 A

[56] References Cited

U.S. PATENT DOCUMENTS

| 605,959 | 6/1898 | Henderson | 248/441 A X |
| 4,047,307 | 9/1977 | Quinn | 35/28 |

*Primary Examiner*—Harland S. Skogquist
*Attorney, Agent, or Firm*—Sughrue, Rothwell, Mion, Zinn and Macpeak

[57] ABSTRACT

A frame for facial identification system in which changeable component segments are assembled in partially overlapping, layered fashion, has a base with a central reservoir therein in which the assembled segments are disposed. A transparent cover plate is hinged at one side of the base, and top hinge plates rest on a ledge of the base, with the cover plate against a cover rim. Clamps on the base are pivoted to engage the cover plate against the rim.

3 Claims, 3 Drawing Figures

U.S. Patent  Sept. 19, 1978  4,114,293
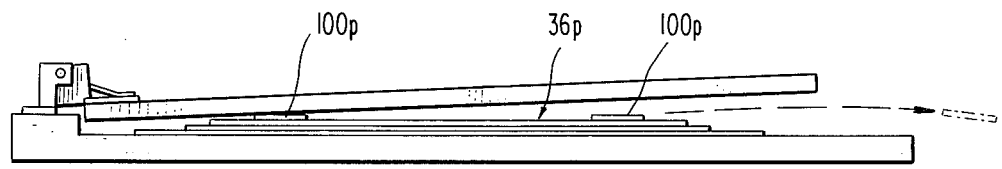
FIG. 1 — PRIOR ART
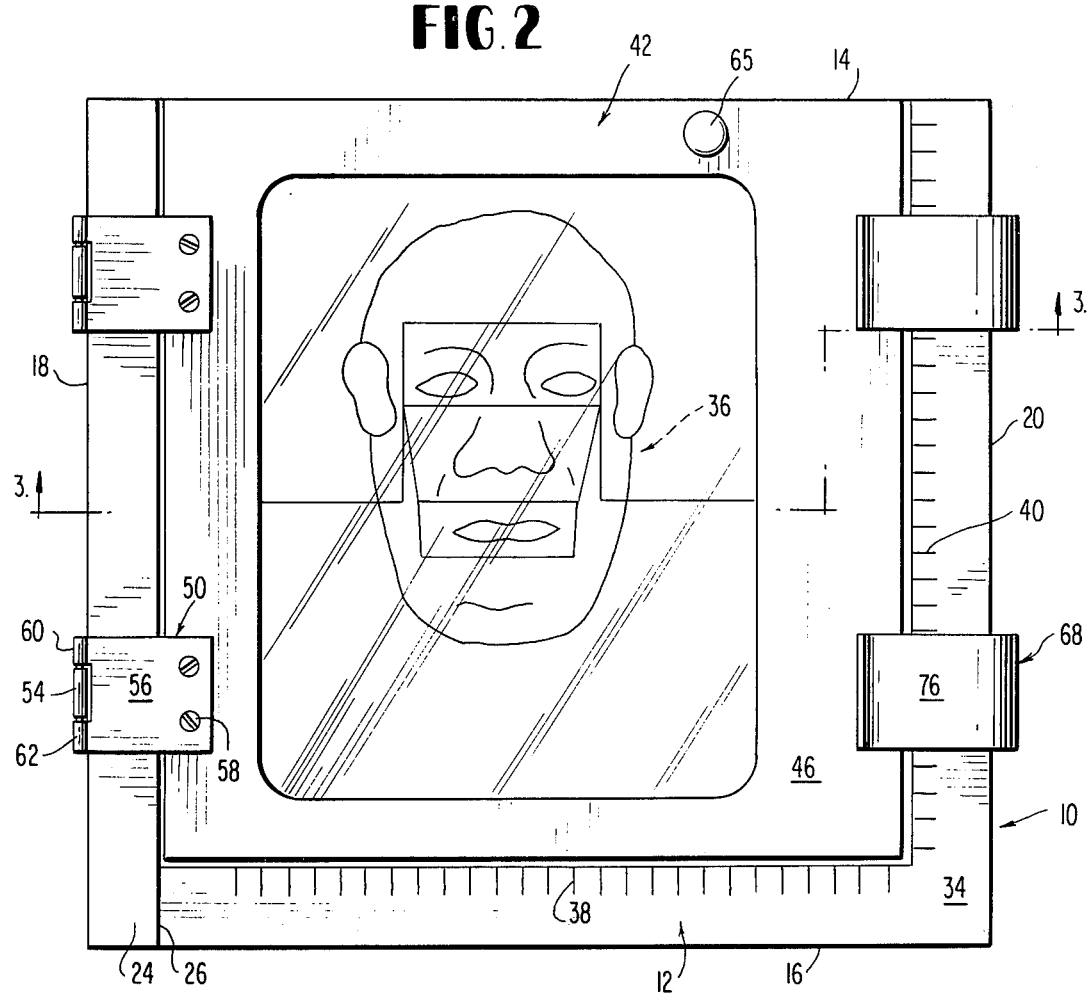
FIG. 2
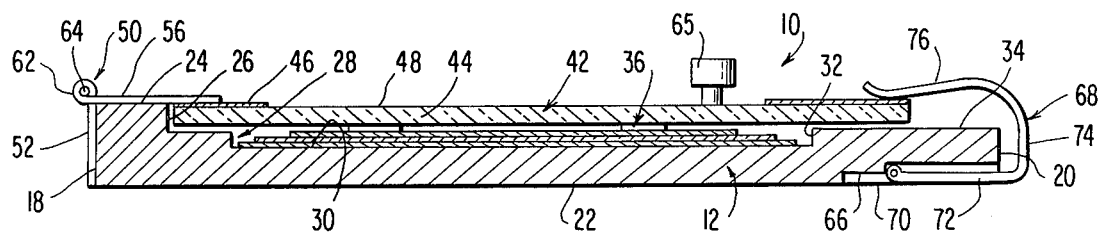
FIG. 3

4,114,293

FRAME FOR FACIAL IDENTIFICATION SYSTEM WITH COMPONENT RESERVOIR

BACKGROUND OF THE INVENTION

1. Field of the Invention

This invention pertains to improvements in frames for holding in assembled condition the component segments of a facial identification system.

2. Statement of the Prior Art

This invention relates generally to that type of apparatus dislcosed in my prior U.S. Pat. No. 3,896,565 and in co-pending U.S. Pat. No. 4,047,307. Facial identification systems including changeable components arranged in overlapped condition are generally in widespread use by investigative agencies and the like. Representative of the prior art problems which this invention seeks to correct is that apparatus shown in FIG. 1 and described in more detail hereinafter.

SUMMARY OF THE INVENTION

In the formation of facial likenesses from component segments, it is necessary that the segments be assembled in somewhat irregular, overlapped condition. In order to maintain the assembled likenesses in the selected position during handling by witnesses and others, various frames have been proposed in which a cover clamps the assembled components against the base. Inasmuch as both the cover and the base are flat, and since the assembled components are of irregular height being made up from a number of pieces, undesirable distortions have occurred after clamping. In order to obviate such distortions, and at the same time to provide a reliable means for maintaining the components in their assembled state, the present invention proposes a stepped base having a reservoir to receive the components. The resevoir is of a depth relative to a surrounding rim such that the height of the assembled components is substantially co-planar with the rim. A cover plate is hinged at one side of the base, and its hinge plate bears against the ledge correctly positioning the cover plate over the reservoir and against the rim and components.

A further objective of the invention resides in the provision of a series of spring clips to releasably engage the cover plate when the latter is in the closed position.

Other and further objects and advantages of the invention will become apparent to those skilled in the art from a consideration of the following specification when read in conjunction with the annexed drawing.

BRIEF DESCRIPTION OF THE DRAWING

FIG. 1 is a side elevational view of a prior art frame showing the problem solved by the invention hereof;

FIG. 2 is a top plan view of a device constructed and assembled in accordance with this invention; and FIG. 3 is a transverse sectional view on line 3—3 of FIG. 2, looking in the direction of the arrows.

DESCRIPTION OF THE PREFERRED EMBODIMENT

Referring to the drawing in more detail, and initially to FIGS. 2 and 3, the holding frame 10 of the present invention has a base 12 comprising a main component thereof. The base 12 has top and bottom edges 14 and 16 and side edges 18 and 20. With minor exceptions noted below, the lower surface 22 of the base is substantially planar, and the upper surfaces are on several planes. Said upper surfaces include a elevated hinge ledge 24 located adjacent the side edge 18 and terminating in an inside wall 26. A depressed central reservoir has a main surface 30, and surrounding wall 32, and is defined by a cover rim support surface about the base and at least one side thereof.

As seen in FIG. 3, the depth of the reservoir is substantially equal to the maximum height of an assembled group of the components, designated herein by reference numeral 36. Thus, the components are substantially co-planar at their maximum upper extremity with the surface 34.

The surface 34 is further provided with coordinate grid marks at 38 and 40 to provide reference locator indicia for facial characteristics.

A cover plate 42 comprises a transparent body member 44 having opaque border covering 46 about its upper surface 48. The cover plate is mounted for disposition over the reservoir 28 in such manner as to maintain the components 36 in assembled condition but to avoid distortion of the image created thereby. To this end, a series of hinge assemblies 50 each including a first hinge portion 52 are secured to the side edge 18, each having a central, tubular hinge sleeve 54 projecting above the level of the ledge member 24. Second hinge plates 56 are secured to the upper surface 48 of the cover plate by fasteners 58 and have spaced apart hinge sleeves 60 and 62. The sleeves 54, 60 and 62 are co-axialy aligned, and a hinge pin 64 extends therethrough.

As shown in FIG. 2, a handle 65 may be provided for lifting of the cover.

Formed in the base 12 and opening on its lower surface 22 along the side edge 20 are a series of shallow slots 66. Secured within these slots are spring clamps 68 comprising clamp hinge plates 70. A clamp arm 72 is pivotally secured to each plate, and is capable of being positioned in co-planar relationship with the surface 22 so that the base may be positioned flush against the supporting surface. At the outer extremity of each arm 72 is a substantially right angular portion 74 to which an integral, recurved spring member 76 is attached. As shown in the drawing, the members 76 extend over to and releasably engage the cover plate.

The advantages flowing from the construction hereof may be noted by comparison of prior art FIG. 1 with invention FIG. 3. In FIG. 1 the assembled components 36p include ears 100p at either side of the subjects likeness. As shown in phantom lines however, as the cover is closed, the differential height of the components prevents the cover from contacting all components, and one of the ears is displaced, thereby distorting the image. Here, such distortion is prevented in the invention apparatus inasmuch as the components are all within the reservoir and displacement is unlikely or impossible.

I claim:

1. In a facial identification system comprising a composite of facial features interrelated to form a representation of a subject, the composite being made up of changeable individual feature component segments which partially overlap one another in irregular layered fashion, a holder for the assembled, partially overlapped segments comprising:

a base member having a planar lower surface, side edges, top and bottom edges, and upper surfaces;

said upper surfaces of said base member including an elevated hinge ledge adjacent one of said side edges, a depressed reservoir surface of a depth and extent to accommodate said assembled, partially overlapped segments, and a cover rim support surface of a height intermediate that of the hinge ledge and the reservoir;

a transparent cover plate moveably mounted for disposition over the central holder surface, and bearing against the cover rim support surface; and releasable clamp means for maintaining said cover plate in position.

2. The invention of claim 1, wherein:

the cover plate is hingedly mounted by hinge means;

the hinge means comprising a plurality of hinges each having a first hinge plate secured to said one of the side edges and having a projecting sleeve;

a second hinge plate secured to the cover plate and having hinge sleeves aligned with the sleeve of the first plate;

hinge pins extending through said sleeve; and the second hinge plate bearing against the hinge ledge when the cover plate is pivoted over the central holder.

3. The invention of claim 2, wherein:

the base member has a series of slots formed in the lower surface thereof;

a clamp arm pivotally secured in each of said slots; and spring clamps on said arms extendable over the cover plate to releasably lock the cover plate in position.

* * * * *